(12) United States Patent
Nishigishi (10) Patent No.: US 8,585,612 B2
(45) Date of Patent: Nov. 19, 2013

(54) GUIDEWIRE (75) Inventor: Makoto Nishigishi, Aichi (JP)

(73) Assignee: Asahi Intecc Co., Ltd., Nagoya-Shi (JP)

( * ) Notice: Subject to any disclaimer, the term of this patent is extended or adjusted under 35 U.S.C. 154(b) by 0 days.

(21) Appl. No.: 13/028,623

(22) Filed: Feb. 16, 2011

(65) Prior Publication Data
US 2011/0208092 A1     Aug. 25, 2011

(30) Foreign Application Priority Data
Feb. 19, 2010  (JP) .................................. 2010-034759

(51) Int. Cl.
A61M 25/00 (2006.01)

(52) U.S. Cl.
USPC ........................................................ 600/585

(58) Field of Classification Search
USPC ........................................................ 600/585
See application file for complete search history.

(56) References Cited

U.S. PATENT DOCUMENTS

| | | | |
|---|---|---|---|
| 5,063,935 A * | 11/1991 | Gambale | 600/585 |
| 5,144,959 A | 9/1992 | Gambale et al. | |
| 5,345,945 A | 9/1994 | Hodgson et al. | |
| 5,365,942 A | 11/1994 | Shank | |
| 5,377,690 A | 1/1995 | Berthiaume | |
| 5,402,799 A | 4/1995 | Colon et al. | |
| 5,833,631 A | 11/1998 | Nguyen | |
| 6,113,557 A | 9/2000 | Fagan et al. | |
| 6,183,420 B1 | 2/2001 | Douk et al. | |
| 6,648,837 B2 | 11/2003 | Kato et al. | |
| 7,077,811 B2 | 7/2006 | Vrba et al. | |
| 7,399,283 B2 | 7/2008 | Kato | |
| 2006/0235337 A1 | 10/2006 | Vrba et al. | |
| 2008/0214959 A1 | 9/2008 | Miyata et al. | |
| 2009/0112127 A1 | 4/2009 | Keating et al. | |

FOREIGN PATENT DOCUMENTS

| | | |
|---|---|---|
| DE | 19823414 A1 | 6/1999 |
| EP | 0815894 A1 | 1/1998 |
| JP | 6501179 T | 2/1994 |
| JP | 2001178829 A | 7/2001 |
| JP | 2006511304 T | 4/2006 |
| JP | 2008161491 A | 7/2008 |
| WO | 2009-054972 A1 | 4/2009 |

OTHER PUBLICATIONS

European Search Report for Application No. 11154500.0 dated May 11, 2011.
European Office Action for 11 154 500 dated Sep. 6, 2012.

* cited by examiner

Primary Examiner — Brian Szmal
Assistant Examiner — H. Q. Nguyen
(74) Attorney, Agent, or Firm — Oliff & Berridge, PLC (57) ABSTRACT An object of the present invention is to provide a guidewire capable of obtaining a sufficient tip load, and also preventing as much as possible a distal portion from being twisted or bent. The guidewire has an outer coil and an inner coil. The outer coil has a taper coil portion with its outer diameter gradually decreasing toward the front end of the core shaft. The inner coil surrounds a distal side portion of the core shaft inside the outer coil. The rear end of the inner coil is joined only to the core shaft on the front side of a position where the taper coil portion of the outer coil has a maximal outer diameter.

7 Claims, 4 Drawing Sheets

GUIDEWIRE

CROSS REFERENCE TO RELATED APPLICATIONS

This application is related to U.S. application Ser. No. 12/973,252 and U.S. application Ser. No. 12/977,121, the entire contents of which are hereby incorporated by reference.

This application is based on Japanese Patent Application No. 2010-034759 filed with the Japanese Patent Office on Feb. 19, 2010, the entire content of which is hereby incorporated by reference.

TECHNICAL FIELD

The present invention relates to a medical guidewire.

BACKGROUND ART

There have conventionally been proposed a variety of guidewires for guiding a catheter or the like, which is used by being inserted into tubular organs such as vessels, digestive tracts and ureters, and intracorporeal tissues, for the purpose of treatment or experiment. For example, there are one formed by doubly providing coils in a distal portion of a core shaft (for example, see Japanese Translation of PCT Publication Nos. 6-501179 and 2006-511304), one formed by using a stranded wire made up of a plurality of strands inside the coil of the distal portion (for example, see Japanese Patent Application Laid-Open No. 2008-161491), and the like.

Further, a guidewire for use in a relatively severe stenotic part of a vessel, typified by a part with stenosis named chronic total occlusion (CTO), needs to pass through a narrow lesion part. For this reason, as this guidewire, there is one having a tapered coil portion in a tip portion of a core shaft, and the tapered coil portion has a coil with a reduced outer diameter in the tip portion (for example, see Japanese Translation of PCT Publication No. 6-501179, FIG. 5, and Japanese Patent Application Laid-Open No. 2001-178829).

SUMMARY OF INVENTION

In order to pass the guidewire through a minute space present in the part with such severe stenosis as chronic total occlusion, it is necessary to reduce an outer diameter of the front end of the guidewire. Therefore, there is often used a guidewire having a coil with an outer diameter of the tip reduced by having a tapered portion as described above.

When such a guidewire is inserted into the minute space present in the stenotic part and then applied with rotational torque from the proximal side, the distal portion of the guidewire is captured by the stenotic part, which may bring the guidewire into a difficult condition to rotate. When further rotational torque is applied to the guidewire in such a condition, a phenomenon called kink in which the distal portion is twisted or bent may occur.

For preventing occurrence of such kink, there is considered enhancing the stiffness of the distal portion of the core shaft. However, with this expedient, the flexibility of the distal portion of the guidewire tends to be impaired, while a tip load of the guidewire also tends to increase to a degree more than necessary.

Herein, the tip load means a maximal load when a tip portion of guidewire pushes a load measurement device in an axial direction until the guidewire buckles.

Further, when such a guidewire is pushed into the stenotic part, the distal portion of the guidewire may be bent to be plastically deformed. That is, in this case, the guidewire is not restored and a residual angle occurs in the guidewire.

As a method for improving restoring force of the guidewire to prevent occurrence of such a residual angle, there is considered reducing a diameter of the distal portion of the core shaft where the residual angle is apt to occur. However, reducing the diameter of the distal portion of the core shaft causes a difficulty to obtain a sufficient tip load.

The present invention has been made in view of such circumstances. An object of the present invention is to provide a guidewire having a desired tip load and capable of preventing as much as possible occurrence of kink in a distal portion of the guidewire even in the case of the distal portion being applied with excess rotational torque due to being captured in a stenotic part, or for some other reason.

Further, another object of the present invention is to provide a guidewire having a desired tip load, and also having improved restoring force of the distal portion.

In the present invention, the above objects are achieved by an aspect described below.

A guidewire in accordance with the present invention includes: a core shaft; an outer coil that has a taper coil portion formed by winding at least one strand such that an outer diameter gradually decreases toward a front end of the core shaft, and surrounds a distal side portion of the core shaft; an inner coil that surrounds the distal side portion of the core shaft inside the outer coil; a tip joint that joins a front end of the outer coil and a front end of the inner coil to the front end of the core shaft; an outer rear end joint that joins a rear end of the outer coil to the core shaft; and an inner rear end joint that joins a rear end of the inner coil only to the core shaft on a front side of a position where the taper coil portion of the outer coil has a maximal outer diameter.

BRIEF DESCRIPTION OF DRAWINGS

The foregoing and other objects, features, aspects and advantages of the invention will become more apparent from the following detailed description when taken in conjunction with the accompanying drawings.

DESCRIPTION OF EMBODIMENTS

Preferred embodiments of the present invention will be described below with reference to the accompanying drawings, in which like reference characters designate similar or identical parts throughout the several views thereof.

<1> A guidewire in accordance with a first aspect of the present invention includes: a core shaft; an outer coil that has a taper coil portion formed by winding at least one strand such that an outer diameter gradually decreases toward a front end of the core shaft, and surrounds a distal side portion of the core shaft; an inner coil that surrounds the distal side portion of the core shaft inside the outer coil; a tip joint that joins a front end of the outer coil and a front end of the inner coil to the front end of the core shaft; an outer rear end joint that joins a rear end of the outer coil to the core shaft; and an inner rear end joint that joins a rear end of the inner coil only to the core shaft on a front side of a position where the taper coil portion of the outer coil has a maximal outer diameter.

<2> A guidewire in accordance with a second aspect of the present invention is the guidewire described in the first aspect, wherein the outer coil has an outer intermediate joint which joins the outer coil to the core shaft between the tip joint and the outer rear end joint, and the inner rear end joint of the inner coil is located on a front side of the outer intermediate joint.

<3> A guidewire in accordance with a third aspect of the present invention is the guidewire described in the first aspect, wherein the outer coil has an open coiled portion with coils of the strand spaced apart from one another on a front side of the outer coil, and also has a close coiled portion with coils of the strand substantially in contact with one another on a rear end side of the outer coil, and the inner rear end joint of the inner coil is located on a rear side of a boundary between the close coiled portion and the open coiled portion.

<4> A guidewire in accordance with a fourth aspect of the present invention is the guidewire described in the first aspect, wherein the outer coil has a tip straight coil portion with a substantially constant outer diameter on a front side of the taper coil portion, and the inner rear end joint of the inner coil is located on a rear side of a boundary between the tip straight coil portion and the taper coil portion.

<5> A guidewire in accordance with a fifth aspect of the present invention is the guidewire described in the fourth aspect, wherein the tip straight coil portion has an open coiled portion with coils of the strand spaced apart from one another on a front side of the tip straight coil portion, and also has a close coiled portion with coils of the strand substantially in contact with one another on a rear end side of the tip straight coil portion.

<6> A guidewire in accordance with a sixth aspect of the present invention is the guidewire described in the first aspect, wherein the inner coil surrounds a portion of the core shaft with minimal flexural stiffness.

<7> A guidewire in accordance with a seventh aspect of the present invention is the guidewire described in the first aspect, wherein the inner coil is a hollow stranded coil, formed by stranding a plurality of strands.

<1> In the guidewire in accordance with the first aspect of the present invention, the outer coil has the taper coil portion with its outer diameter decreasing toward the tip. Thereby, the outer diameter of the front end of the guidewire is made small. This enables the front end of the guidewire to enter a narrow stenotic part, and also to further proceed inside the stenotic part while gradually spreading the stenotic part by the taper coil portion. The distal portion of the core shaft is surrounded by the inner coil on the front side of the position where the taper coil portion has the maximal outer diameter. Therefore, the presence of the inner coil decreases a space between the distal portion of the core shaft and the outer coil. It is thereby possible to realize a structure which resists occurrence of distortion in the distal portion of the core shaft. Accordingly, even with excess rotational torque applied to the guidewire, occurrence of kink in the distal portion of the guidewire can be prevented as much as possible.

Further, due to the inner coil being present, a desired tip load can be obtained. This can reduce the diameter of the distal portion of the core shaft. For this reason, restoring force of the distal portion of the guidewire improves. Accordingly, it can be prevented as much as possible that, at the time of pushing the guidewire into the stenotic part, the guidewire is bent in the distal portion to be plastically deformed, and is not restored with a residual angle generated therein.

<2> In the second aspect of the present invention, the inner rear end joint of the inner coil is located on the front side of the outer intermediate joint, while not being joined to the outer intermediate joint. This can prevent as much as possible an abrupt change in stiffness of the guidewire. For this reason, rotational force and pushing force applied from the proximal side of the guidewire can be efficiently transmitted to the front side. That is, torque transmissibility is improved in this guidewire.

Further, the inner coil surrounds the core shaft on the front side of the outer intermediate joint. Therefore, a portion where the stiffness is increased by the inner coil can be restricted to the distal portion of the core shaft which is conventionally apt to be bent. Moreover, the space is formed between the inner rear end joint and the outer intermediate joint. Thereby, this space functions so as to maintain the flexibility of the core shaft and eliminate the increase in stiffness made by the inner coil. It is thus possible to maintain the flexibility of the distal portion of the guidewire.

<3> In the third aspect of the present invention, the outer coil has the open coiled portion on the front side. Hence the structure of the guidewire becomes one with high safety and more flexibility toward the tip. Further, even in the case of the outer coil and the inner coil coming into contact with each other, due to the open coiled portion of the outer coil being present, the strand of the outer coil is allowed to make slight movement. This eliminates the interference of the outer coil with the inner coil, thereby maintaining the flexibility of the distal portion of the guidewire.

Moreover, the inner rear end joint of the inner coil is located on the rear side of the boundary between the close coiled portion and the open coiled portion. Hence the guidewire of this aspect is configured such that the inner rear end joint does not agree with the boundary between the close coiled portion and the open coiled portion where a change occurs in stiffness. For this reason, an abrupt change in stiffness of the guidewire can be prevented as much as possible. Accordingly, the rotational force and the pushing force applied from the proximal side of the guidewire can be efficiently transmitted to the front side. That is, the torque transmissibility is improved in this guidewire.

<4> In the fourth aspect of the present invention, the outer coil has the tip straight coil portion on the front side of the taper coil portion. Therefore, an overlapping portion of the inner coil and the outer coil increases. This also enables the guidewire to easily enter a narrow stenotic part. This can further prevent distortion from occurring in the distal portion of the core shaft. Accordingly, even when excess rotational torque is applied to the guidewire, it is possible to further prevent occurrence of kink in the distal portion of the guidewire.

Moreover, the inner rear end joint of the inner coil is located on the rear side of the boundary between the tip straight coil portion and the taper coil portion. Hence the guidewire of this aspect is configured such that the inner rear end joint does not agree with the portion where a change occurs in stiffness due to the difference in outer diameter of the outer coil. For this reason, an abrupt change in stiffness of the guidewire can be prevented as much as possible. Accordingly, the rotational force and the pushing force applied from the proximal side of the guidewire can be efficiently transmitted to the front side. That is, the torque transmissibility is improved in this guidewire.

<5> In the fifth aspect of the present invention, the tip straight coil portion has the open coiled portion on the front side. Hence the structure of the guidewire becomes one with high safety and more flexibility toward the tip.

Further, even in the case of an increase in portion where the outer coil and the inner coil are in contact with each other due to overlapping thereof, bending of the outer coil and slight movement of the strand of the outer coil are allowed due to the open coiled portion being present. This eliminates the interference of the outer coil with the inner coil, thereby maintaining the flexibility of the distal portion of the guidewire.

<6> In the sixth aspect of the present invention, the inner coil surrounds the portion of the core shaft with minimal flexural stiffness, where kink is apt to occur. Therefore, the outer diameter of the inner coil can be further reduced. Further, as a consequence, the outer diameter of the distal portion of the outer coil can also be further reduced.

It is to be noted that the portion of the core shaft with minimal flexural stiffness normally corresponds to a portion of the core shaft with a minimal outer diameter, or the thinnest portion formed by flattening the portion of the core shaft with a reduced diameter by pressing or the like.

<7> In the seventh aspect of the present invention, the inner coil is the hollow stranded coil formed by stranding a plurality of strands. By use of such a coil, a high effect can be obtained for improving the tip load while maintaining the flexibility of the tip portion of the guidewire. Hence it is possible to further reduce the diameter of the tip portion of the core shaft. This can more effectively prevent the residual angle from occurring in the guidewire due to bending of the guidewire.

Moreover, the use of the stranded coil improves the torque transmissibility of the tip portion of the guidewire.

Figure 1:
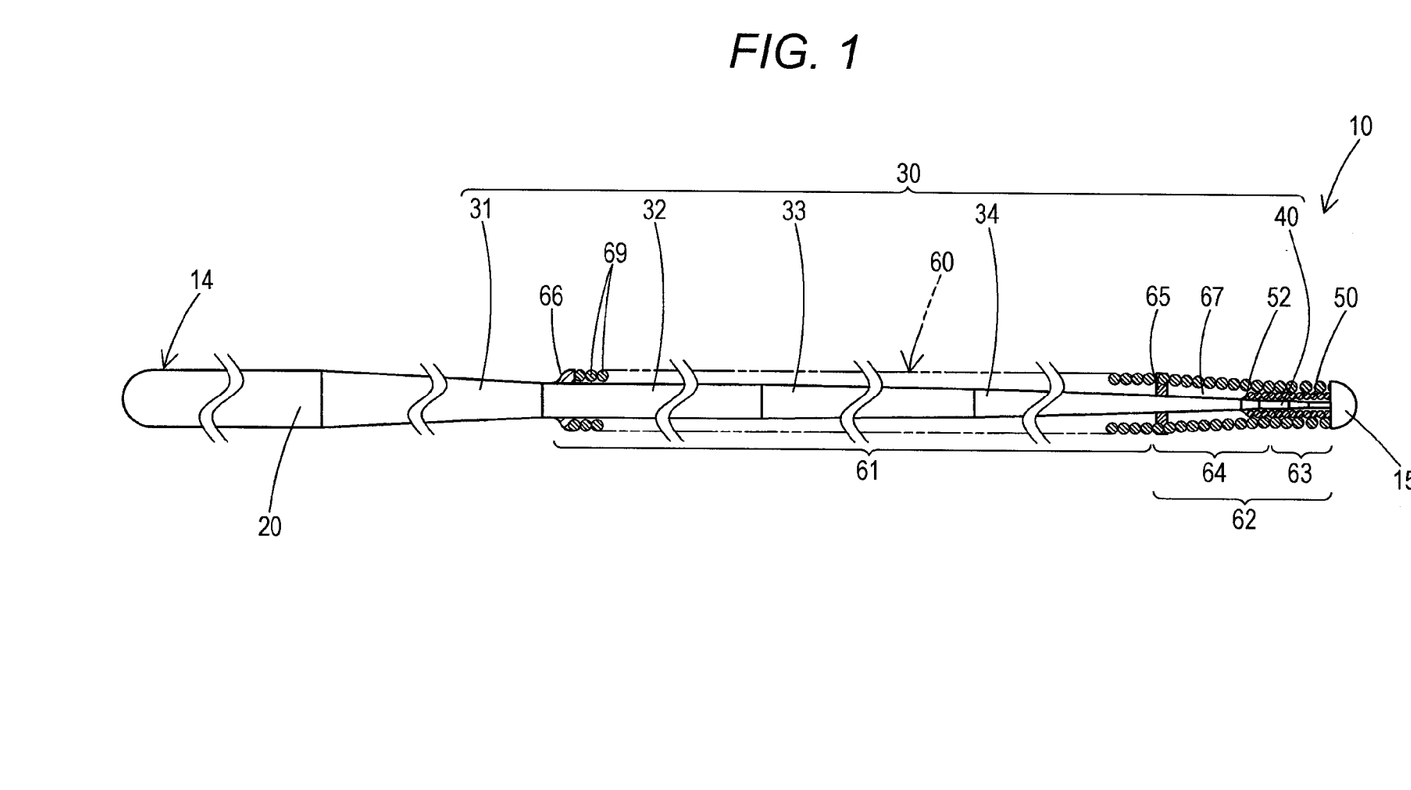
FIG. 1 illustrates an overall view of a guidewire of the present embodiment.
Figure 2:
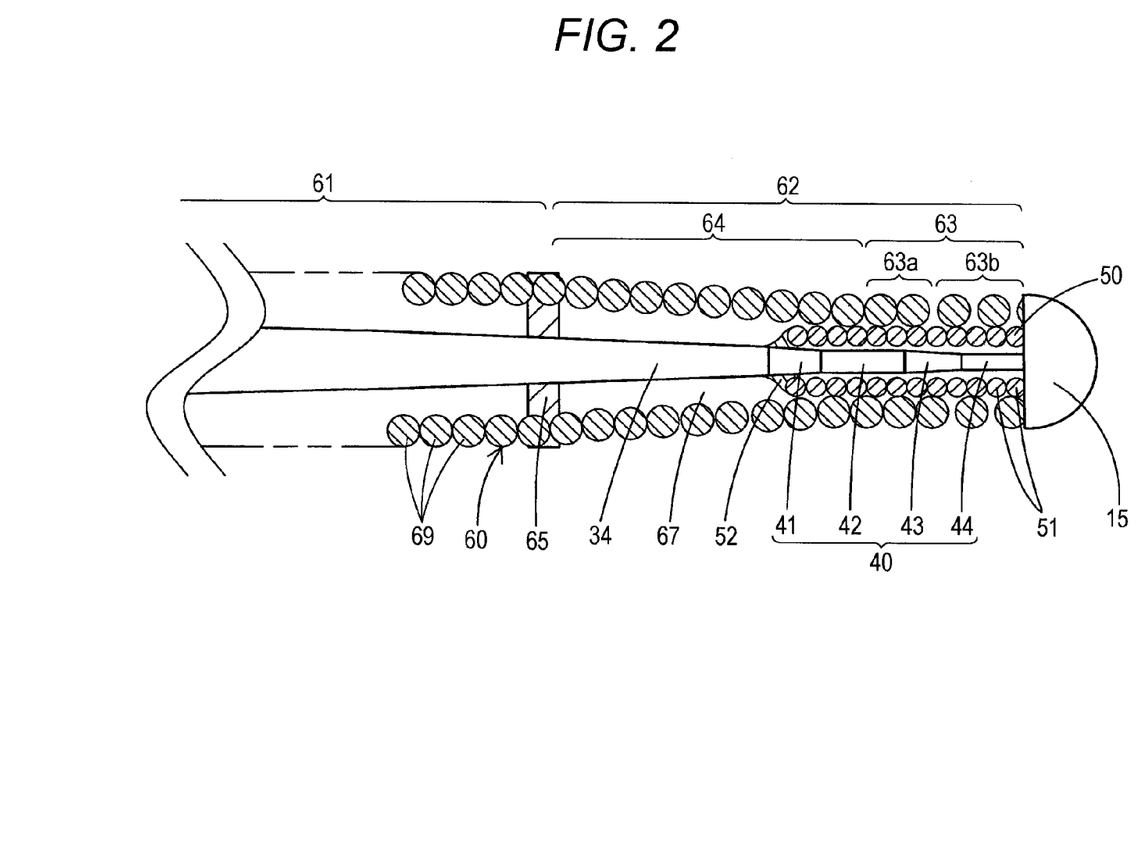
FIG. 2 illustrates a partially enlarged view of FIG. 1.

A guidewire of the present embodiment will be described with reference to FIGS. 1 and 2. In FIGS. 1 and 2, the right side shown is the front side (distal side) to be inserted into a body, and the left side is the rear end side (proximal side, base end side) to be operated by an operator.

A guidewire 10 is principally used for treatment of a vessel in the heart. The guidewire 10 has a length of about 1900 mm in the case of the present embodiment.

The guidewire 10 is principally made up of a core shaft 14, an inner coil 50 and an outer coil 60. The core shaft 14 is roughly divided into a body portion 20 and a distal side portion 30. The outer surface of the guidewire 10 from the tip to a predetermined range of the body portion 20 over the outer coil 60 has been subjected to hydrophilic coating.

The distal side portion 30 is a portion formed by reducing a diameter of the core shaft 14. In the case of the present embodiment, a length of the distal side portion 30 is about 260 mm. The body portion 20 is a portion in cylindrical shape with a constant diameter, and takes up the portion other than the distal side portion 30. In the case of the present embodiment, a diameter of the body portion 20 is set to about 0.35 mm.

A material for the core shaft 14 is not particularly limited, but in the case of the present embodiment, stainless steel (SUS304) is used. As the material other than this, a super elastic alloy such as Ni—Ti alloy, a piano wire, or the like is used.

The distal side portion 30 has a first taper part 31, a small diameter part 32, a second taper part 33, a third taper part 34, and a most distal portion 40 in this order from the body portion 20 toward the front end of the guidewire 10.

In the case of the present embodiment, the first taper part 31 has an axial length of about 95 mm. The first taper part 31 is a tapered portion having a circular cross section. In the present embodiment, the diameter of the first taper part 31 decreases from about 0.35 mm to about 0.21 mm in the direction toward the tip.

The small diameter part 32 is a cylindrical portion having a circular cross section and a certain diameter. In the case of the present embodiment, a diameter of the small diameter part 32 is about 0.21 mm.

The second taper part 33 and the third taper part 34 are tapered portions having different inclination angles and circular cross sections. In the case of the present embodiment, a diameter decreases from about 0.21 mm to about 0.05 mm from the end of the proximal side of the second taper part 33 to the end of the front side of the third taper part 34.

The arrangements and dimensions of the foregoing first to third taper parts 31, 33, 34 and the small diameter part 32 can be changed as appropriate for the purpose of obtaining desired stiffness, or some other purpose. For example, a cylindrical portion having a constant diameter can be provided between the second taper part 33 and the third taper part 34. Further, the number and angles of the taper parts can also be set as appropriate.

As shown in FIG. 2, the most distal portion 40 has a first taper flexible part 41, a first columnar flexible part 42, a second taper flexible part 43, and a second columnar flexible part 44 in this order from the third taper part 34 toward the front end of the guidewire 10. In the present embodiment, an axial length of the most distal portion 40 is set to about 16 mm.

The most distal portion 40 is a portion with a particularly low flexural stiffness in the core shaft 14. Above all, the second columnar flexible part 44 is a portion with a minimal flexural stiffness.

The first taper flexible part 41 and the second taper flexible part 43 are tapered portions having circular cross sections. The first columnar flexible part 42 and the second columnar flexible part 44 are cylindrical portions having circular cross sections as well as constant diameters.

The first taper flexible part 41 is configured such that its diameter decreases from the distal end of the third taper part 34 toward the first columnar flexible part 42. In the case of the present embodiment, a diameter of the first columnar flexible part 42 is set to about 0.045 mm.

The second taper flexible part 43 is configured such that its diameter decreases from the distal end of the first columnar flexible part 42 toward the proximal side of the second columnar flexible part 44. A diameter of the second columnar flexible part 44 is set to about 0.04 mm.

The inner coil 50 is attached to the distal portion of the core shaft 14 so as to surround a total length of the most distal portion 40. The inner coil 50 is a hollow stranded coil, manufactured by closely stranding a plurality of metal-made strands 51 on a core so as to be substantially in contact with one another, removing residual stress generated at the time of the stranding by means of a known thermal treatment, and then pulling out the core. In the case of the present embodiment, an outer diameter of the inner coil 50 is about 0.09 mm.

In the case of the present embodiment, six strands 51 are used for the inner coil 50. A diameter of the strand 51 is about 0.02 mm.

Although a material for the strand 51 is not particularly limited, in the case of the present embodiment, stainless steel is employed. As a material other than this, a super elastic alloy such as Ni—Ti alloy is used. Further, strands made of different materials may also be combined.

The number of strands 51 is not particularly limited, either, and can be set as appropriate in accordance with an after-mentioned desired tip load.

It is to be noted that, for the sake of facilitating understanding, the diameter of the strand 51 of the inner coil 50 and a diameter of a strand 69 of the outer coil 60 described later, shown in FIGS. 1 and 2, are emphasized in illustration as compared with dimensions of the core shaft 14.

The front end of the inner coil 50 is joined by brazing to the front end of the core shaft 14 coaxially with respect to an axial line of the core shaft 14, along with the front end of the outer coil 60. This brazed portion forms a substantially hemispherical tip plug (tip joint) 15.

The rear end of the inner coil 50 is joined by brazing to the first taper flexible part 41 of the most distal portion 40. This brazed portion forms an inner rear end joint 52.

The inner coil 50 serves to prevent kink of the guidewire 10 (namely, twisting or bending of the distal portion of the guidewire 10 during operation). Hence it is preferable that the inner coil 50 at least surround the most distal portion 40 where the kink is apt to occur and the flexural stiffness is low with a reduced diameter. Concerning the guidewire for use in the case of a relatively severe stenosis of a vessel, typified by the part with stenosis named chronic total occlusion (CTO), as in the guidewire 10 of the present embodiment, a portion within about 30 mm from the front end of the guidewire is preferably surrounded by the inner coil 50. Further, the range surrounded by the inner coil 50 substantially agrees with a range where a conditioning called shaping is performed in which the distal portion of the core shaft 14 is previously bent in a predetermined direction.

Most of the core shaft 14 from the most distal portion 40 to the small diameter part 32 is inserted inside the outer coil 60. The outer coil 60 is formed by winding one metal-made strand 69, and made up of a coil body portion 61 and a distal coil portion 62.

The coil body portion 61 is a portion wound by the strand 69 so as to have a constant outer diameter. In the case of the present embodiment, the outer diameter of the coil body portion 61 is about 0.36 mm, and an axial length thereof is about 120 mm. In the coil body portion 61, adjacent coils of strand 69 are closely wound so as to be substantially in contact with each other.

The distal coil portion 62 has a taper coil portion 64 on the rear end side, and also has a tip straight coil portion 63 on the front side.

The taper coil portion 64 is a portion wound by the strand 69 such that its outer diameter decreases toward the tip. In the case of the present embodiment, the outer diameter of the taper coil portion 64 decreases from about 0.36 mm to about 0.2 mm. An axial length of the taper coil portion 64 is about 30 mm. In the taper coil portion 64, the adjacent coils of the strand 69 are closely wound so as to be substantially in contact with each other.

The tip straight coil portion 63 is a portion wound by the strand 69 so as to make its outer diameter constant. In the case of the present embodiment, an outer diameter of the tip straight coil portion 63 is about 0.2 mm, and an axial length thereof is about 10 mm. The tip straight coil portion 63 has on the rear end side thereof a close coiled portion 63*a* which is closely wound such that the adjacent coils of the strand 69 are substantially in contact with each other, and also has on the front side thereof an open coiled portion 63*b* which is openly wound such that a space is present between the adjacent coils of the strand 69. The open coiled portion 63*b* enhances the flexibility of the distal portion of the outer coil 60. Further, as described later, the open coiled portion 63*b* alleviates the interference between the outer coil 60 and the inner coil 50.

The strand 69 of the outer coil 60 is made up of a radiopaque metal wire such as platinum alloy. In the case of the present embodiment, a diameter of the strand 69 is about 0.055 mm.

It is to be noted that the strand 69 of the outer coil 60 may be made up of one strand obtained by joining a radiopaque metal wire such as platinum alloy with a radiolucent metal wire made of stainless steel or the like. For example, about 30 mm of the front side of the outer coil 60 may be formed of the radiopaque coil, while the remaining rear end side may be formed of the radiolucent coil.

As apparent from the outer diameter of the tip straight coil portion 63, the diameter of the strand 69 and the outer diameter of the inner coil 50, the inner peripheral surface of the tip straight coil portion 63 and the outer peripheral surface of the inner coil 50 are substantially in contact with each other. These are arranged so as to form almost no space therebetween.

The front end of the outer coil 60 is joined by brazing to the front end of the core shaft 14, coaxially with the inner coil 50 to form the tip plug 15. The rear end of the outer coil 60 is joined by brazing to the small diameter part 32. This brazed portion forms an outer rear end joint 66.

Further, the outer coil 60 is joined by brazing to the third taper part 34 at the rear end of the taper coil portion 64. This brazed portion forms an outer intermediate joint 65.

It is to be noted that the outer intermediate joint 65 is preferably located inside the taper coil portion 64. However, the outer intermediate joint 65 does not necessarily need to agree with the rear end of the taper coil portion 64. As described later, the position of the outer intermediate joint 65 is not particularly limited as long as it is a position where the outer intermediate joint 65 and the inner rear end joint 52 of the inner coil 50 are spaced apart from each other by a predetermined distance.

The foregoing inner rear end joint 52 of the inner coil 50 is arranged on the rear side of the proximal end of the close coiled portion 63*a* of the tip straight coil portion 63 of the outer coil 60, and on the front side of the outer intermediate joint 65. With such an arrangement, an abrupt change in stiffness of the guidewire 10 due to the inner rear end joint 52 of the inner coil 50 being present can be prevented as much as possible. That is, the tip straight coil portion 63 of the outer coil 60 has the open coiled portion 63*b* openly winding the strand 69 and the close coiled portion 63*a* closely winding the strand 69. For this reason, a stiffness change occurs at a boundary between this open coiled portion 63*b* and the close coiled portion 63*a*. Similarly, since an outer shape of the outer coil 60 changes at a boundary between the tip straight coil portion 63 and the taper coil portion 64, a stiffness change occurs in the outer coil 60. When the boundaries at which the stiffness changes occur as thus described are overlapped with the inner rear end joint 52 of the inner coil 50, it results in enhancement of the stiffness change. To prevent this, the inner rear end joint 52 is preferably displaced from the boundary between the open coiled portion 63*b* and the close coiled portion 63*a* in the tip straight coil portion 63, and from the boundary between the tip straight coil portion 63 and the taper coil portion 64, as described above. Accordingly, the inner rear end joint 52 is displaced to the rear side of the boundary between the tip straight coil portion 63 and the taper coil portion 64 (namely, the rear side of the proximal end of the close coiled portion 63*a* of the tip straight coil portion 63).

It is to be noted that in the case of the outer coil 60 having a structure where the tip straight coil portion 63 is not included, the open coiled portion is provided on the front side of the taper coil portion 64 and the close coiled portion is provided on the rear end side of the taper coil portion 64, the inner rear end joint 52 is preferably displaced to the rear side of the boundary between the open coiled portion and the close coiled portion.

Further, the inner coil 50 is arranged between the most distal portion 40 of the core shaft 14 and the tip straight coil portion 63 of the outer coil 60. Further, as described above, the inner coil 50 is arranged so as to be substantially in contact with the tip straight coil portion 63. Hence in the most distal portion 40 of the core shaft 14, the coil structure with a radial space made as small as possible.

Although the inner coil 50 has the flexibility, the inner coil 50 and the outer coil 60 may substantially come into contact and thus interfere with each other, thereby to cause deterioration in flexibility of the outer coil 60. However, the outer coil 60 is provided with the open coiled portion 63b having spaces between the coils of the strand 69. This allows the outer coil 60 to be bent, and the coils of the strand 69 to slightly move in the axial direction. It can thus be prevented as much as possible that the inner coil 50 interferes with the outer coil 60 and the flexibility of the outer coil 60 is thus lost.

Meanwhile, the coils of the strand 69 are allowed to move in the axial direction due to the open coiled portion 63b of the outer coil 60 being present. Therefore, at the time of operating the guidewire 10, disproportionate arrangement of the coils of the outer coil 60 in one direction (so-called pitch displacement of the coil) may occur. However, the open coiled portion 63b is arranged on the tip straight coil portion 63 so as to be substantially in contact with the inner coil 50. Accordingly, occurrence of excess pitch displacement is prevented as much as possible.

Further, the inner rear end joint 52 of the inner coil 50 is spaced apart from the outer intermediate joint 65 of the outer coil 60 in the axial direction. A space 67 is thus formed between both the joints. When the inner coil 50 and the outer coil 60 are jointed to the core shaft 14 at the same position, the stiffness of the guidewire 10 at that position becomes high. This leads to an abrupt change in stiffness of the guidewire 10. Therefore, in order to prevent such a change in stiffness as much as possible, the space 67 is provided. With this configuration, it is possible to improve the transmissibility of the rotational force and the pushing force applied from the proximal side of the guidewire 10.

Further, the space 67 between the inner rear end joint 52 of the inner coil 50 and the outer intermediate joint 65 of the outer coil 60 also contributes to improvement in flexibility of the guidewire 10. That is, adopting the double coil structure made up of the inner coil 50 and the tip straight coil portion 63 increases the stiffness in the most distal portion 40 of the core shaft 14, whereby the flexibility of the guidewire 10 may deteriorate. To prevent this, the space 67 without the inner coil 50 is provided, thereby maintaining the flexibility of the guidewire 10.

Therefore, even when the inner coil 50 is arranged in the tip straight coil portion 63 of the outer coil 60, due to the open coiled portion 63b and the space 67 being present as described above, the core shaft 14 is allowed to be flexed, and deterioration in flexibility of the guidewire 10 is prevented as much as possible.

To form the space 67, the inner rear end joint 52 of the inner coil 50 is preferably spaced apart from the outer intermediate joint 65 by 5 mm or longer in the axial direction. Further, at least a space not smaller than the diameter of the strand 51 of the inner coil 50 is preferably provided in a radial direction of the core shaft 14 to the inner surface of the inner coil 50.

Two kinds of guidewires were produced based on the above configuration. An experiment was then conducted on an influence exerted by the presence of the inner coil 50 having the foregoing configuration upon kink resistance of the guidewire. The kink resistance indicates resistance to occurrence of plastic deformation such as twisting or bending of the guidewire in the case of continuously rotating the guidewire. In a test for determining the kink resistance, the tip plug portion of the guidewire was non-rotatably fixed, and the proximal side of the guidewire was rotated in the same direction at a constant rate. The number of rotations was then counted until a state occurred where the guidewire was subjected to plastic deformation such as twisting or bending, and was not restored.

As a comparative guidewire, the guidewire 10 of the present embodiment without the inner coil 50 was used. Herein, the tip load as a maximal axial load to act on the tip portion needs to be equivalently set between the two guidewires. The tip load is an important indicator for the guidewire to show influences upon the property of the guidewire to proceed without being bent even when coming into contact with a stenotic part, and upon a sense of an operator at the time of seeking a minute space present in the stenotic part. Therefore, as the comparative guidewire, there was used a guidewire having a slightly larger diameter of a core shaft which corresponds to the portion corresponding to the most distal portion 40 than that of the guidewire 10 of the present embodiment by a space for the inner coil 50 not provided, but having an equivalent tip load to the guidewire 10 of the present embodiment.

Figure 3:
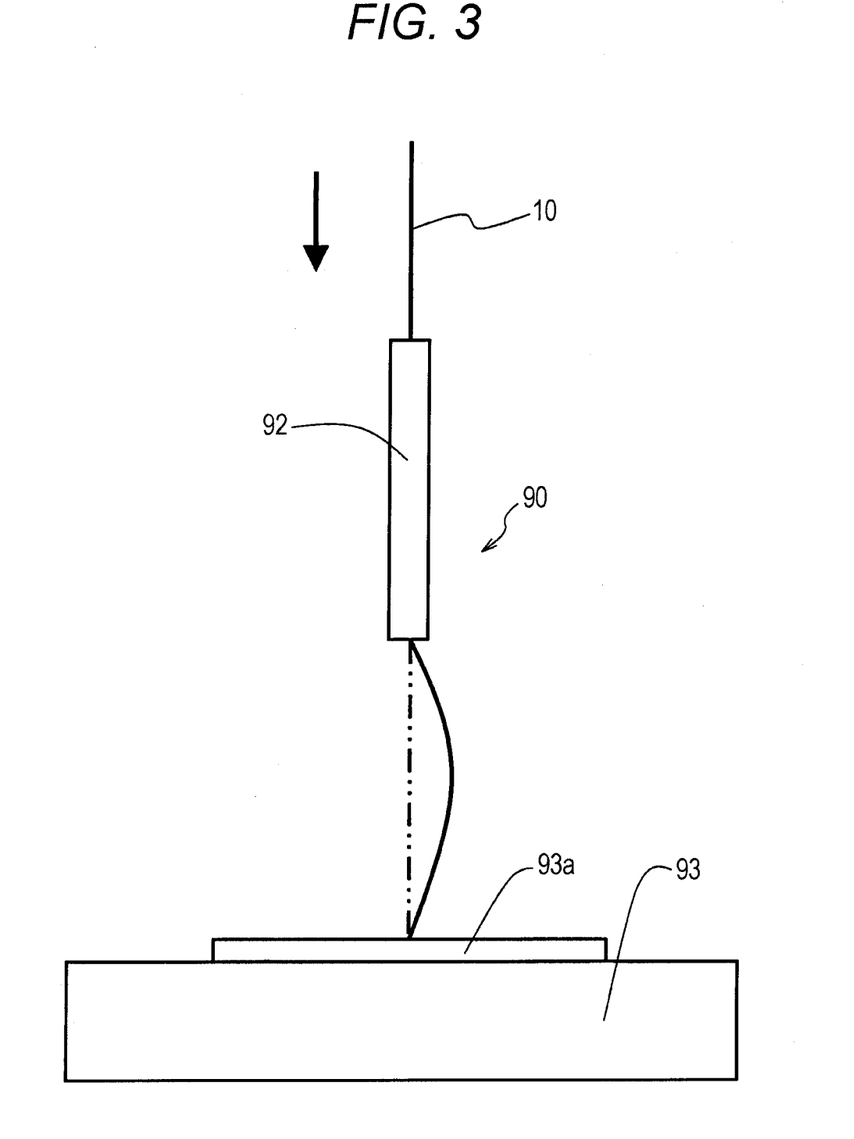
FIG. 3 illustrates a view of an apparatus for measuring a tip load of the guidewire.

FIG. 3 schematically illustrates a measurement device 90 for measuring a tip load. In the present embodiment, the tip load was set to about 5.0 [mN].

The measurement device 90 is configured to have a measurement portion 93a on a load measurement device 93, and a cylindrical supporting portion 92 for supporting a guidewire, which is arranged above the measurement portion 93a. In measurement by the measurement device 90 having such a configuration, first the guidewire is inserted into the supporting portion 92. Subsequently, the guidewire is substantially vertically placed such that the front end of the guidewire is in contact with the measurement portion 93a. In this state, the measurement portion 93a is pressed downward by the front end of the guidewire. A maximal load at this pressing is measured as the tip load.

With such a method, the comparative guidewire and the guidewire 10 of the present embodiment, having substantially the same tip load, were prepared. Subsequently, as described above, the tip plug portion of the guidewire was fixed and the proximal side was rotated in the same direction at a constant rate, thereby to measure the kink resistance of each of the guidewires.

As a consequence, the conventional comparative guidewire was kinked after 2.5 rotations. To the contrary, the guidewire 10 of the present embodiment was not kinked even after eight or more rotations. It thus became apparent that this guidewire 10 had improved kink resistance.

One of the causes of this is considered to be that, in the guidewire 10 of the present embodiment, the inner coil 50 is provided in the space between the distal portion of the core shaft 14 and the outer coil 60, and this space thus decreases, whereby the guidewire 10 is structured to resist occurrence of distortion in the distal portion of the core shaft 14 which causes the kink.

As described above, the guidewire 10 of the present embodiment has the taper coil portion 64 of the outer coil 60, thus reducing the outer diameter of the outer coil 60. Hence the guidewire 10 can enter a relatively severe, narrow stenotic part. Further, the guidewire 10 has a structure where the most distal portion 40 is surrounded by the inner coil 50. The guidewire 10 can thus have improved kink resistance without impairing the tip load despite having the outer diameter of the thin distal portion. That is, the guidewire 10 is prevented from being twisted or bent even in the case of being further applied with rotational torque from the proximal side when entering a stenotic part inside a vessel to become non-rotatable.

Further, in the guidewire 10, the inner coil 50 is arranged as spaced apart from the outer intermediate joint 65 of the outer coil 60. Further, the inner rear end joint 52 is arranged as displaced to the rear side of the boundary between the tip straight coil portion 63 and the taper coil portion 64. Therefore, the abrupt change in stiffness of the guidewire 10 is prevented as much as possible. Accordingly, the rotational torque and the axial pushing torque applied from the proximal side of the guidewire 10 can be effectively transmitted. That is, the torque transmissibility is improved in the guidewire 10.

Further, in the guidewire 10, the tip load can be increased by the inner coil 50. Hence the diameter of the most distal portion 40 of the core shaft 14 can be reduced. Therefore, the restoring force of the distal portion of the guidewire can be improved while the tip load is maintained at a desired value. It is thus possible to provide a guidewire with high restoring force with occurrence of a residual angle prevented as much as possible.

In the present embodiment described above, the inner coil 50 is configured of stranded coil made up of the plurality of strands 51. However, the inner coil 50 may be a single-wire coil made up of one strand though the tip load, the kink resistance and the torque transmissibility may not be improved as much as those of the stranded coil as described above. Even in the case of being the single-wire coil, the inner coil 50 is preferably a closely wound coil where adjacent coils of strand are substantially in contact with each other.

Moreover, in the present embodiment, it is described that the outer coil 60 is made up of the three portions: the coil body portion 61, the taper coil portion 64, and the tip straight coil portion 63. However, the outer coil 60 may be configured not to have the tip straight coil portion 63, but to be provided with a coil portion tapered to the tip.

Figure 4:
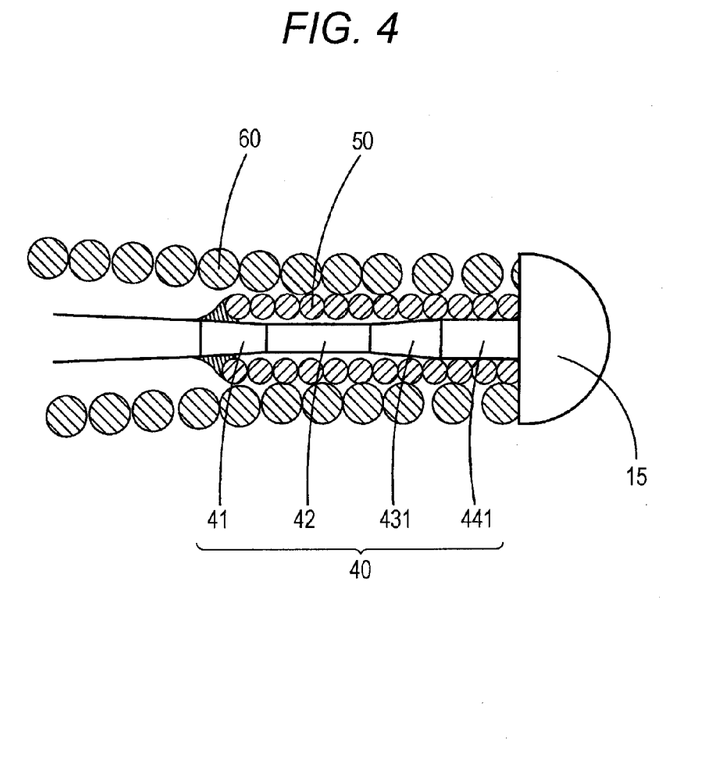
FIG. 4 illustrates a guidewire of another embodiment.

In the embodiment described above, it is described that the most distal portion 40 is made up of the first taper flexible part 41, the first columnar flexible part 42, the second taper flexible part 43 and the second columnar flexible part 44, and any of these portions has a circular cross section. However, this is not restrictive, and the distal portion of the most distal portion 40 may be configured to have one or a plurality of flat portions formed by pressing or the like. For example, as shown in FIG. 4, the portions corresponding to the foregoing second taper flexible part 43 and second columnar flexible part 44 may be modified to a portion 431 having a pair of inclined planes and a plate-like flat portion 441.

In this manner, providing the distal portion processed by pressing or the like in the most distal portion 40 can give the effect of enhancing the flexibility and the torsional stiffness of the most distal portion 40. In such a configuration, the flattened portions 431 and 441 have minimal flexural stiffness, though having directional properties due to having been flattened. It is preferable that the inner coil 50 at least surround these flattened portions 431 and 441.

Further, the guidewire of the present embodiment is applicable not only to a heart, but also to a brain or other organs.

While the invention has been shown and described in detail, the foregoing description is in all aspects illustrative and not restrictive. It is therefore understood that numerous modifications and variations can be devised without departing from the sprit and scope of the invention.

The invention claimed is:

1. A guidewire, comprising:
   a core shaft;
   an outer coil that surrounds a front side portion of the core shaft and has a taper coil portion formed by winding at least one strand such that an outer diameter of the taper coil portion gradually decreases toward a front end of the core shaft;
   an inner coil that surrounds the front side portion of the core shaft inside the outer coil;
   a tip joint that joins a front end of the outer coil and a front end of the inner coil to the front end of the core shaft;
   an outer rear end joint that joins a rear end of the outer coil to the core shaft; and
   an inner rear end joint that joins a rear end of the inner coil only to the core shaft on a front side from a position where the taper coil portion of the outer coil has a maximal outer diameter, wherein the maximal diameter of the taper portion is less than a maximal diameter of the outer coil.

2. The guidewire according to claim 1, wherein
   the outer coil has an outer intermediate joint which joins the outer coil to the core shaft between the tip joint and the outer rear end joint, and
   the inner rear end joint of the inner coil is located on a front side from the outer intermediate joint.

3. The guidewire according to claim 1, wherein
   the outer coil has an open coiled portion with coils of the strand spaced apart from one another on a front side of the outer coil, and also has a close coiled portion with coils of the strand substantially in contact with one another on a rear end side of the outer coil, and
   the inner rear end joint of the inner coil is located on a rear side of a boundary between the close coiled portion and the open coiled portion.

4. The guidewire according to claim 1, wherein
   the outer coil has a tip straight coil portion with a substantially constant outer diameter on a front side of the taper coil portion, and
   the inner rear end joint of the inner coil is located on a rear side of a boundary between the tip straight coil portion and the taper coil portion.

5. The guidewire according to claim 4, wherein the tip straight coil portion has an open coiled portion with coils of the strand spaced apart from one another on a front side of the tip straight coil portion, and also has a close coiled portion with coils of the strand substantially in contact with one another on a rear end side of the tip straight coil portion.

6. The guidewire according to claim 1, wherein the inner coil is a hollow stranded coil, formed by stranding a plurality of strands.

7. The guidewire according to claim 2, wherein the inner coil is a hollow stranded coil, formed by stranding a plurality of strands.

* * * * *